United States Patent [19]
Pratt et al.

[11] Patent Number: 5,814,049
[45] Date of Patent: Sep. 29, 1998

[54] PROCESS FOR APPLYING SUCTION TO BONE DRILLING AND REAMING OPERATIONS

[75] Inventors: Clyde Pratt, Somis; Roger Carignan, Camarillo, both of Calif.

[73] Assignee: Kinamed, Inc., Newbury Park, Calif.

[21] Appl. No.: 549,482

[22] Filed: Oct. 27, 1995

[51] Int. Cl.⁶ .................................................. A61B 17/16
[52] U.S. Cl. ................................ 606/80; 606/79; 606/85; 606/84
[58] Field of Search ......................................... 606/79–85

[56] References Cited

PUBLICATIONS

"Primary Reamed Intramedullary Nailing Of Open Femoral Shaft Fractures," Clinical Orthopaedics And Related Research, No. 318, pp. 182–190.
"Measurement Of Femoral Vein Blood Flow During Total Hip Replacement," The Journal Of Bone And Joint Surgery, vol. 76–B, No. 6, Nov. 1994, pp. 919–921.
"Postoperative Surveillance For Deep Venous Thrombosis With Duplex Ultrasonography After Total Knee Arthroplasty," The Journal Of Bone And Joint Surgery, vol. 76–A, No. 11, Nov. 1994, pp. 1649–1657.
"A Venous Foot Pump Reduces Thrombosis After Total Hip Replacement," The Journal Of Bon And Joint Surgery, vol. 74–B, No. 1, Jan. 1992, pp. 45–49.
"The Clinical Course Of Distal Deep Venous Thrombosis After Total Hip and Total Knee Arthroplasty, As Determined With Duplex Ultrasonography," The Journal Of Bone And Joint Surgery, vol. 76–A, No. 11, Nov. 1994, pp. 1658–1663.

*Primary Examiner*—Michael Buiz
*Assistant Examiner*—Daphna Shai
*Attorney, Agent, or Firm*—Oppenheimer Poms Smith

[57] ABSTRACT

The tool of the present invention comprises a stem. Cutting teeth extend outward from the stem. The stem has a central, longitudinal passage, connects to a suction or evacuation line. An outlet of the passage is at or near the cutting site. As material is cut, the suction carries the material to the central passage where it is evacuated. In one embodiment, each tooth has a cutting edge and a back side. One or more tubes connect the central passage to the back side of the cutting teeth. Suction from the central passage acts on the tubes to create suction at the cutting site. In another embodiment, the central passage is open at the distal end of the tool. Suction at the distal end cut material toward the distal end of the tool and into the central passage where it is evacuated from the tool.

14 Claims, 3 Drawing Sheets

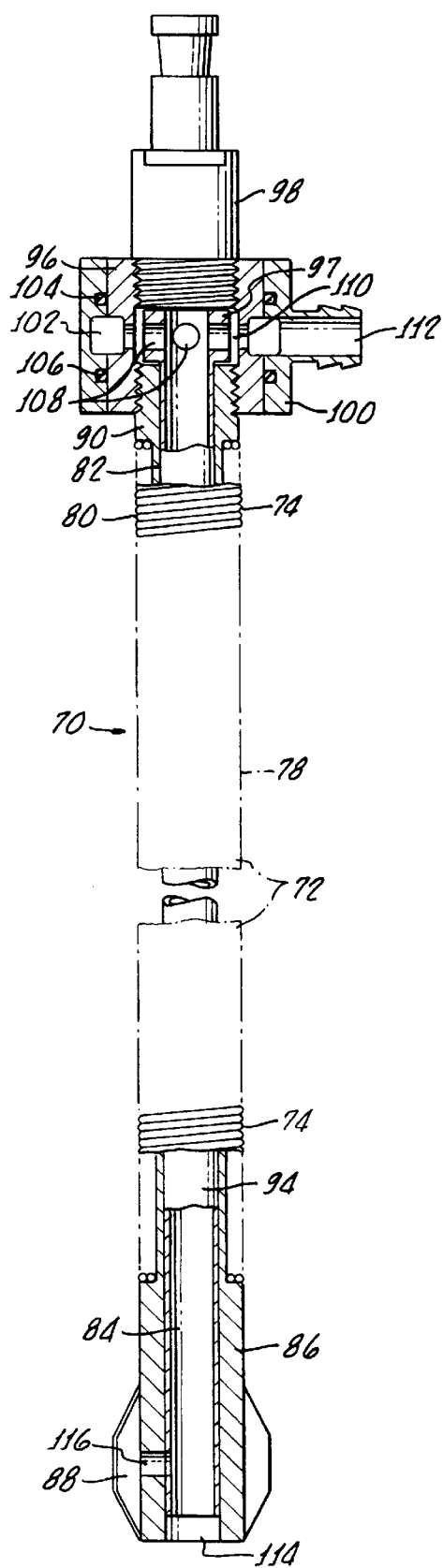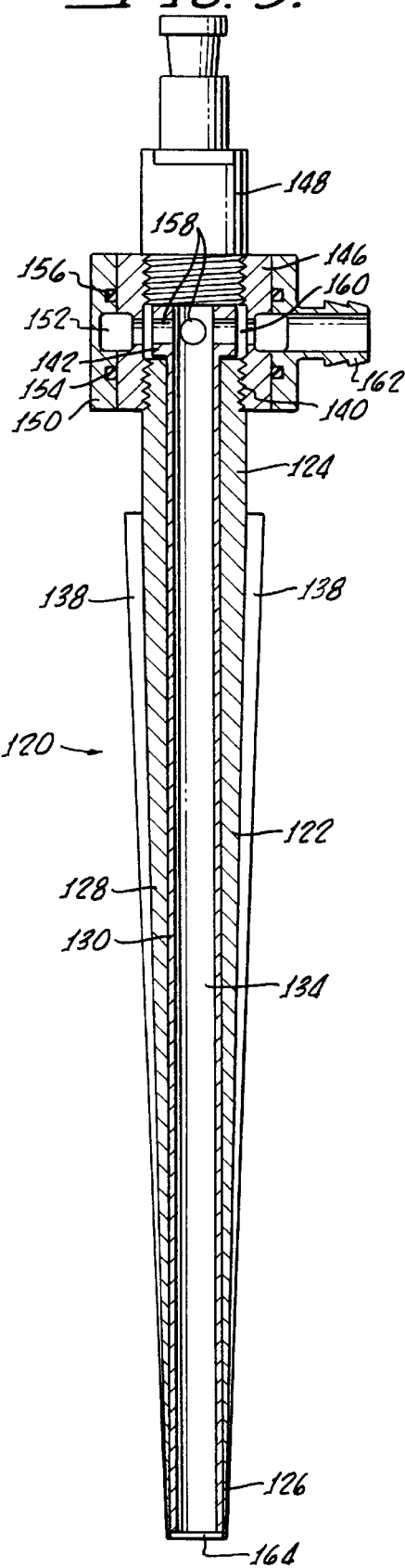

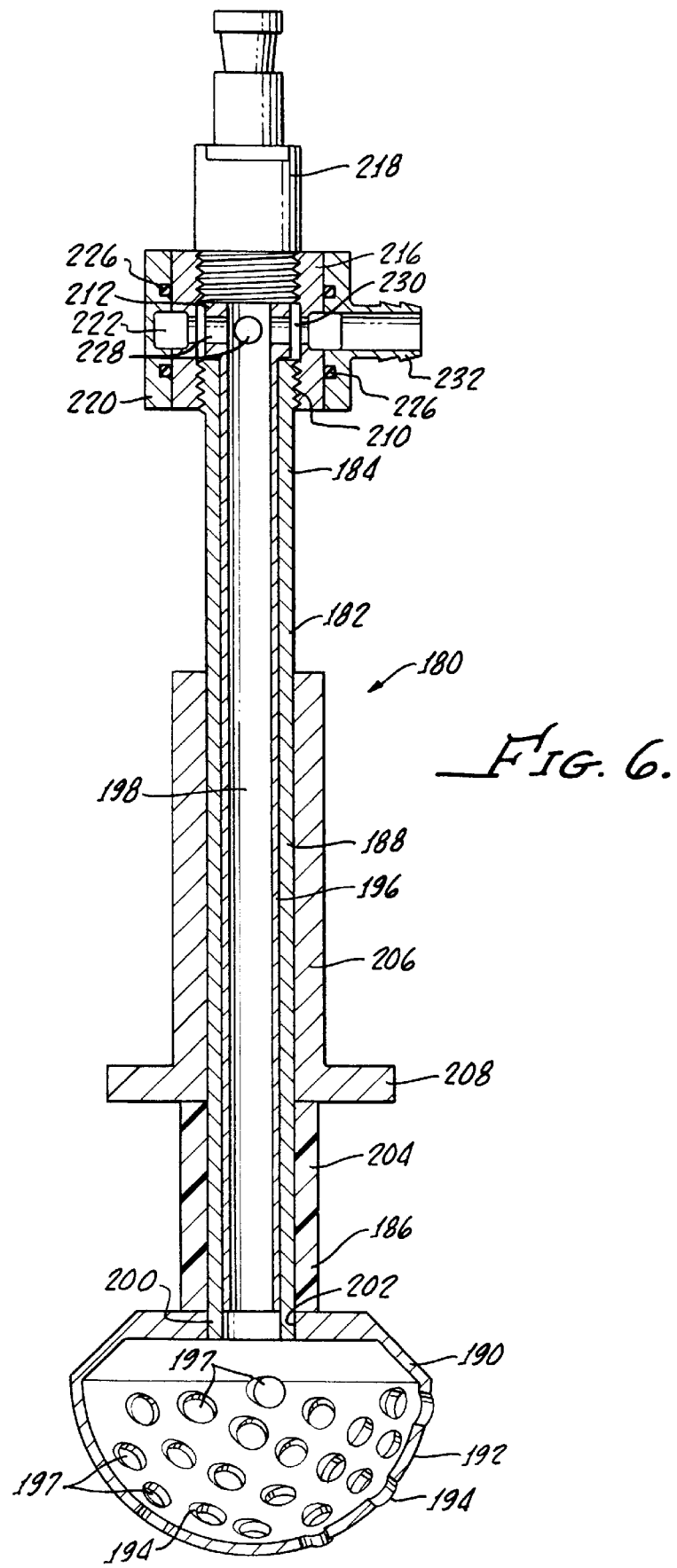

PROCESS FOR APPLYING SUCTION TO BONE DRILLING AND REAMING OPERATIONS

BACKGROUND OF THE INVENTION

1. Field of the Invention

The present invention relates to a surgical process and tools for the process. In particular, the present invention involves surgeries in which bone and marrow tissue is cut or crushed and removed using broaches, drills, cutters or reaming tools.

2. State of the Art

Orthopedic surgery in which bone tissue is cut or crushed and removed is very common. This occurs during trauma based surgery, fracture fixation and, frequently, total joint replacement. For example, during hip replacement surgery, the surgeon typically cuts into the exposed proximal end of the femur with a broach and removes tissue to a predetermined depth from the femoral canal to accommodate a prosthesis stem. Bone removal also occurs from the pelvis so that a surgeon can attach an acetabular cup.

Kinamed, Inc. of Newbury Park, Calif., publishes a "Surgical Technique Reference Chart" describing how the femur and pelvis are prepared during surgery. That chart is incorporated by reference. ATH broaching tools, which Kinamed manufactures, are some of the available broaching tools that can remove bone tissue from the proximal femur to accommodate the prosthesis stem. Kinamed also manufactures acetabular reaming tools. Other tools can also be used for different procedures such as knee replacement and intramedullary nailing.

For hip replacement surgery, broaching of the femur begins with a narrow T-broach. The T-handle broach primarily identifies the medullary canal axis, and the surgeon uses it to begin opening the canal. Although hand broaches are commonly used, the surgeon can use a rotating broach connected to a drill. Next, the surgeon typically opens the medial aspect of the greater trochanter using a box chisel.

The surgeon next uses a femoral broach. The ATH femoral broach connects to a handle. The surgeon strikes the handle with a mallet to drive the broach into the medullary canal. Teeth on the outside of the broach shear off a layer of small particles of bone and other marrow elements including fat. Small vessels are also cut or separated. After the surgeon drives the broach as far a possible into the canal, the broach is removed to pull out much cut, crushed, or torn tissue from the medullary canal. The surgeon then uses progressively larger broaches to enlarge the opening and remove additional tissue. Eventually the surgeon uses the final size broach to remove the remaining tissue. The surgeon's aim is to obtain an appropriate envelope for the prosthesis to fit within. After broaching, the surgeon removes all extraneous tissue and cleans the remaining bone with pulsating saline lavage and/or $CO_2$ lavage. A suction tube may be employed to remove liquid, blood and debris from the medullary canal.

Prior art material-removing tools and the tool of the present invention have sharp cutting teeth. For example, broaches, which remove material from the medullary canal, typically have a series of horizontal cutting teeth extending from near the proximal end of the tool to the tool's distal end. Each tooth also extends around the broach. As the surgeon forces the tool into the medullary canal, the cutting edge of the tooth cuts, shears, and crushes the tissue within the medullary canal. The cut tissue is forced into the space between the tooth's cutting surface and the back side of the tooth immediately distal to the first mentioned tooth. Of course, all teeth are cutting, and the cut material collects between adjacent teeth. After the broach is inserted as far as possible, the surgeon removes the broach. In the process, the broach carries with it cut tissue. Significant amounts of cut tissue and debris remain, however, within the open cancellous bone matrix situated within the medullary canal.

Several studies recognize a higher than predicted number of postoperative complications including death or much longer hospital stays from this type of surgery. Oishi, C.S., et al., "The Clinical Course of Distal Deep Venous Thrombosis after Total Hip and Total Knee Arthroplasty, as Determined with Duplex Ultrasonography, *Jour. of Bone and Joint Surgery*, Vol. 76-A, No. 11, pg. 1658 (1994), recognized that deep venous thrombosis remains a frequent complication after total joint arthroplasty.

Many believe that deep venous thrombosis can cause a pulmonary embolism. Between 1% and 2% of postoperative patients die from a pulmonary embolism after this type of surgery. Grady-Benson, J. C., et al., "Postoperative Surveillance for Deep Venous Thrombosis with Duplex Ultrasonography after Total Knee Arthroplasty, *Jour. of Bone and Joint Surgery*, Vol. 76-A, No. 11, pg. 1649 (1994), report similar results.

Fordyce, M. J. F., et al, "A Venous Foot Pump Reduces Thrombosis after Total Hip Replacement, *Jour. of Bone Joint Surg.* [Br], Vol. 74-B, No. 1, pg. 45 (1992), describes a foot pump to reduce thrombosis for this type of surgery. Last, Warwick, D., "Measurement of Femoral Vein Blood Flow During Total Hip Replacement," *Jour. Bone Joint Surg.* [Br.]. Vol 76-B, No. 6 (1994) discusses the uses of a foot pump. It notes that researchers found particulate debris traveling proximally through the femoral vein in several total hip replacement patients. The authors were unsure of the debris' significance, however. They noted that some studies had found similar particulate matter in the heart during or immediately after total hip replacement surgery. The particulate matter comprises mixed emboli of bone marrow and thrombotic material.

Thus, although the orthopedic surgical community recognizes that a problem exists in postoperative complications during total joint replacement, trauma surgery, and intramedullary nailing, clinical efforts have been directed towards minimizing the effects of thrombosis through, inter alia, warfarin or fractionated heparin, rather than preventing the causal element of the initiation of thrombosis.

Applicants believe that the particulate matter created by the bone preparation process, such as fat emboli and bone tissue fragments, enter the bloodstream through the venous reservoir in long bones. As the tools cut and crush the boney tissue and marrow of the intramedullary canal, they sever many small vessels. Despite efforts to clean all particulate material away, many particles remain within the cancellous bone matrix. These particles are subsequently forced from the cancellous matrix into the venous reservoir of the bone especially when pressure is applied from within the medullary canal. That pressure is generated either by a device, such as an intramedullary nail or prosthesis stem, an instrument such as an intramedullary alignment rod, or by bone cement when pressurized within the canal. Once within the venous reservoir, the particles are transported throughout the circulatory system where they can do great harm.

SUMMARY OF THE INVENTION

An object of the present invention is to disclose and provide a process and tool for preventing or minimizing particulate matter entering the blood stream during these types of surgeries. Another object of the present invention is to prevent or minimize the particulate matter problem for different tools so that a surgeon can use multiple tools during a surgery without creating problems during use of a particular tool. These and other objects will become apparent in the detailed description of the invention.

Applicants' proposed solution to the particulate problem is to remove the particles as they are created. Applicants accomplish particulate removal by applying suction at or immediately adjacent to the cutting site to remove most particulate matter as it is created.

The tool of the present invention comprises a stem. Cutting teeth extend outward from the stem. The stem has a central, longitudinal passage at least partially through the stem. The passage is connected to a suction or evacuation line so that the central passage is at reduced pressure. An outlet of the passage is at or near the cutting site. As material is cut, the suction carries the material to the central passage. In one embodiment, each tooth has a cutting edge and a back side. One or more tubes connect the central passage to the back side of the cutting teeth. Suction from the central passage acts on the tubes to create suction at the cutting site. The suction pulls the cut particles through the tubes and into the central passage where they are evacuated. In another embodiment, the central passage is open at the distal end of the tool. At least some of the cutting takes place at the distal end. Suction at the distal end, therefore, pulls cut material toward the distal end of the tool and into the central passage where it is evacuated from the tool. Although the evacuation line and central opening primarily provides suction, it also can deliver pulsating lavage or $CO_2$ gas for cleaning. Valves may be employed to control the amount of suction in a given area.

These arrangements are possible for different types of cutting tools. For rotating ones, the design must accommodate a rotating tool and a stationary suction hose. The present invention uses a rotating manifold arrangement to allow for tool rotation. The rotating cutting tool of the present invention has a bearing at the proximal end of the cutting tool. The tool has a manifold between the bearing and the cutting tool. The manifold is operably connected to the central passage, and the evacuation line is connected to the bearing and communicates with the manifold. The manifold transfers the low pressure from the evacuation line to the cutting tool.

BRIEF DESCRIPTION OF THE DRAWINGS

FIGS. 4, 5 and 6 are side sectional views of different rotating tools that utilize the present invention's concepts and teachings.

DETAILED DESCRIPTION OF THE PREFERRED EMBODIMENT

Figure 1:
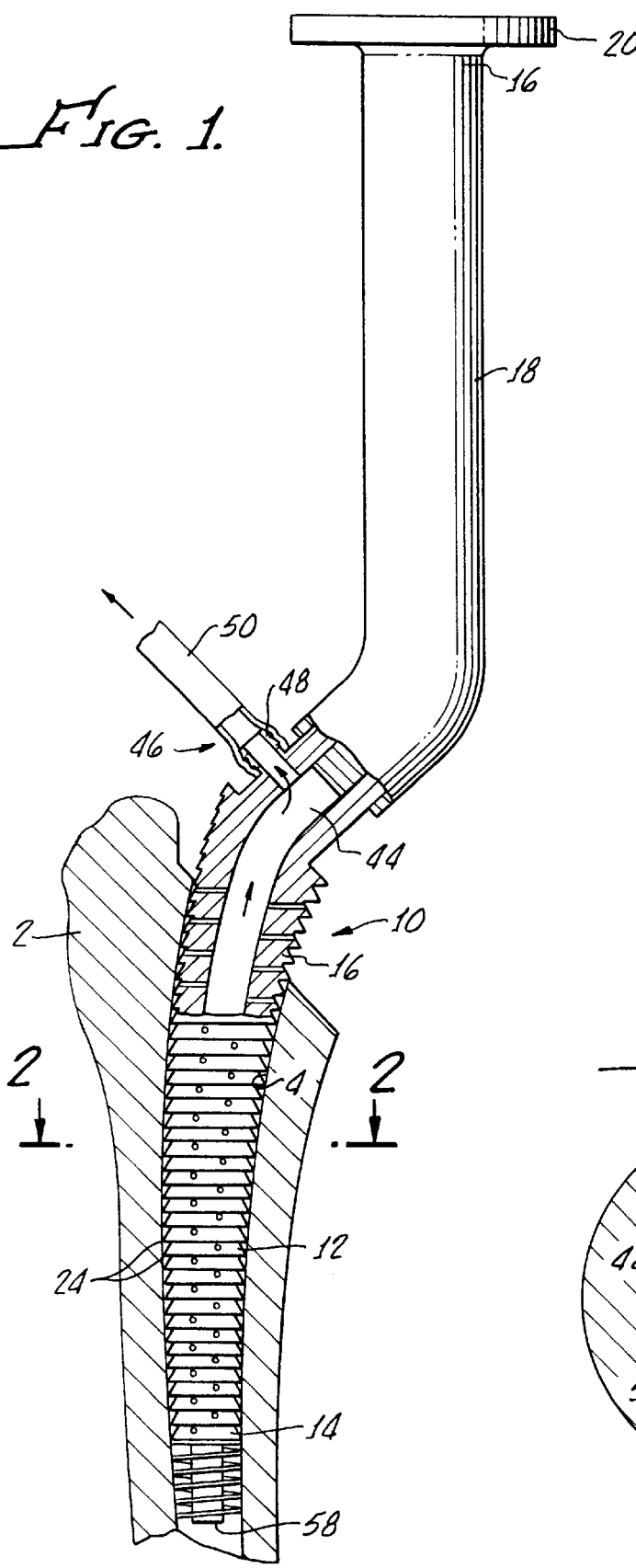
FIG. 1 is a side elevation, partially in section of the broach configuration cutting tool of the present invention. The broach is shown within a proximal femur.
Figure 2:
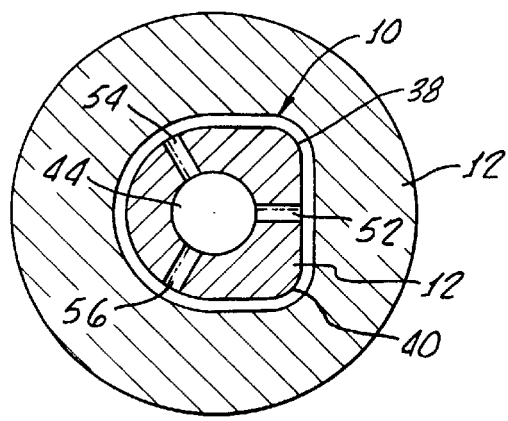
FIG. 2 is a sectional view taken through plane 2—2 in FIG. 1.

The cutting tool of the present invention is shown in its FIG. 1 exemplary embodiment as broach 10. The broach has a stem 12, which, in use, extends into the medullary canal 4 of the proximal femur 2 (FIGS. 1 and 2). A broach handle 18, which, has an anvil surface 20 (FIG. 1), attaches to the proximal end 16 of broach 10.

In use, the surgeon inserts the broach into the medullary canal after some of the softer tissue is removed from the proximal end of the femur. The broach that FIG. 1 shows is close to a largest broach that will be used for the particular femur 2. That is, its outside shape conforms closely to the harder cortical bone's surface around the medullary canal. Typically, the surgeon starts with smaller broaches and uses larger sizes until reaching and using the final, largest size.

Figure 3:
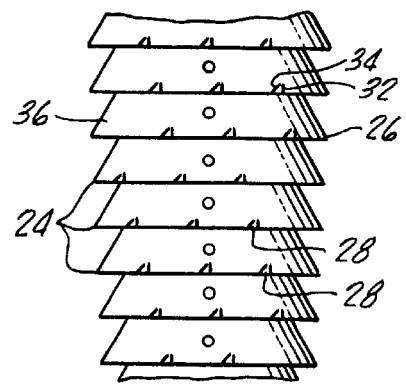
FIG. 3 is a detailed view of a portion of the broach of FIG. 1.

With whatever broach surgeons use, they insert it properly into the medullary canal and then strike anvil surface 20 with a mallet (not shown). This drives the broach deeper into the medullary canal. Cutting teeth 24 on stem 12 (FIGS. 1 and 3) extend outward from the stem. Each tooth 24 has a cutting edge 26 and a back side 36 (FIG. 3). The surface of back side 36 intersects the tooth's cutting edge 26 at a 60° angle. FIG. 2, which does not show the teeth, shows that the corners 38 and 40 of stem 12 are rounded. The teeth at the corners also are rounded.

As FIG. 3 shows, the cutting edge 26 is generally perpendicular to the broach's direction of travel (vertical in FIG. 3) when the surgeon strikes anvil surface 20. As the broach 10 moves, the teeth cut, crush, tear and otherwise remove tissue from within the medullary canal. Preferably, each tooth 24 has spaced notches 28 (FIG. 3). Typically, the notches are about 0.15" (0.3.8 mm) (metric conversions are approximate) apart. Each notch 28 has a generally vertical edge 32 and an angled edge 34, which preferably is 45° to the vertical edge. The tooth pitch preferably is 0.125" (3.18 mm).

As the surgeon drives broach 10 into the medullary canal, the cutting edge scrapes soft material and dislodges it. The broach also crushes and tears other tissue. Notches 28 help break up the tissue. The notches are staggered (FIG. 3) to prevent a "grooving" effect that aligned notches could create. As cutting continues, the dislodged tissue is pushed against the back side 36 of each cutting tooth. It is believed that some small particles of this dislodged material are forced into the cancellous bone matrix where they are subsequently pushed into the venous reservoir where the blood stream transports them away.

To remove this material as it is being cut, applicants' invention has a central passage that leads partially through the stem. In the FIG. 1 exemplary embodiment, central passage 44 generally conforms to the shape of stem 12 (FIGS. 1 and 2). In FIG. 1, the distal end 58 of central opening 44 is open at the distal end 14 of the stem. The central opening is closed at the proximal end of the stem.

An evacuation line 46 in the form of a nipple 48 and a hose 50 communicate with central passage 44. The central passage also communicates with the cutting region. That is, three radial passages, tubes 52, 54, and 56 in this embodiment, extend from central passage 44 to the back side 36 of each tooth. The FIG. 2 exemplary embodiment has three such tubes per tooth. They are cylindrical in the exemplary embodiment, but they may also be flared or have other shapes. The tubes must have a large enough diameter that they will not clog when removed tissue particles pass through the tubes. Further, although FIG. 2 shows three such tubes for each tooth, one could choose a different number.

The surgeon using broach 10 connects hose 50 to a suction or vacuum pump (not shown). This lowers the pressure within central passage 44 and creates suction pulling through tubes 52, 54 and 56. As the surgeon strikes anvil surface 20 and drives broach 10 into the soft tissue, the scraped tissue begins collecting on the back side 36 of each tooth 24. Suction at the outside ends of tubes 52, 54 and 56 draws the cut material inside the tubes and into the central passage 44. From there, the suction pulls the material through central passage 44 and into hose 50 to the pump.

Having an open, distal end 58 of central passage 44 is an option. The suction created there will removed dislodged tissue immediately distal to the broach, but it may adversely affect the suction at the end of tubes 52, 54 and 56.

While broach 10 is still in the medullary canal, (FIG. 1), one can use pulsating lavage or $CO_2$ gas cleaning. To do so, the surgeon removes hose 50 from nipple 48 and connects the nipple to another hose (not shown), which attaches to a liquid or gas line. Liquid or gas would then flow through central passage 44 and out the distal end of passage 58 and tubes 52, 54, and 56.

Different surgical tools also can utilize the process of applicants' invention. FIG. 4 shows one such tool, a reaming tool 70. The tool has a stem 72 extending from a proximal end 74 to a distal end 76. Stem 72 is a two-piece housing 74. Outer, cylindrical housing 78 is tightly wound spring 80. The spring imparts flexibility to the stem so that the distal end 76 of tool 70 can be in a different axis than the proximal end 74. This arrangement allows the tool to reach body parts that might be difficult to reach if stem 72 were rigid.

Stem 72 (FIG. 4) also includes an inner housing 82. The inner housing is flexible to bend as the outer housing bends, and the material chosen will hold low pressure. Alternatively, the inner housing may have a flexible liner 94 of plastic, rubber or other tubing material. The outer housing 78 may be made sufficiently resistant to gas flow so that outside air is not drawn into central passage 84 (FIG. 4) if suction is applied to the central passage. Inner housing 82 could be made of material other than flexible material if it has joints or other provisions that allow for some longitudinal bending.

The distal end of inner housing 82 (FIG. 4) connects to spindle 86, or the inner housing and spindle form a single piece. Outer housing 78 also connects to the spindle. Spindle 86 has radially projecting teeth 88 in this embodiment. The teeth in the FIG. 4 exemplary embodiment have trapezoidal shapes, but they can have different shapes to accomplish cutting of different surfaces.

The proximal end of inner housing 82 is a threaded fitting 90. When the tool parts are assembled, cap 92 at the top of liner 94 rests on top of fitting 90. Fitting 90 threads into rotor 96, and an upper fitting 98 threads into the upper portion of rotor 96.

An evacuation housing 100 surrounds rotor 96. Bearings 102 (FIG. 4) permit rotor 96 to rotate relative to evacuation housing 100. O-rings 104 and 106 seal rotor 96 from evacuation housing 100. Radial openings 108 in cap 102 communicate with central passage 84. The region around cap 92 becomes a manifold 110. Finally, nipple 112, which is part of the evacuation housing 100, communicates with manifold 110 and with a hose (not shown) that attaches to a suction pump.

In use, upper fitting 98 attaches to a drill, motor, handle or other means for providing rotation to the tool. As the tool rotates, teeth 88 remove tissue. When nipple 112 connects to a suction pump through a hose, the manifold 110, holes 108 and central passage 84 are under low pressure. Tissue that teeth 88 cut will be drawn to the distal end 114 of central passage 84 where suction will remove the particles from the cutting site.

Alternatively, tubes such as tube 116 (FIG. 4) can pass from the central passage through spindle 86 to the outer surface of the spindle between adjacent cutting teeth 88. With that alternative embodiment, suction from central passage 88 pulls cut particles from between adjacent cutting piece 88 into central passage 84 where they are disposed of.

Again, instead of applying suction at nipple 112, the hose can connect to a pressurized fluid such as $CO_2$ gas for internal cleaning of the just-cut region.

FIG. 5 shows a different embodiment of a reaming tool 120. The tool has a stem 122 extending from a proximal end 124 to a distal end 126. Stem 122 is a two-piece housing having an outer, cylindrical housing 128 and an inner housing 130 (FIG. 5). The inner housing surrounds a central passage 134.

The outer housing 128 has radially projecting teeth 138. The teeth in the FIG. 5 exemplary embodiment are triangles but they can have different shapes to accomplish cutting of different surfaces. In FIG. 5, the teeth project more radially outward proximally and taper distally.

The proximal end of outer housing 128 is threaded at 140. When the tool is assembled, cap 142 at the top of inner housing 130 rests on top of the threaded end 140 of the outer housing 128. The outer housing threads into rotor 146. Likewise, an upper fitting 148 threads into the upper portion of rotor 146.

An evacuation housing 150 surrounds rotor 146 (FIG. 5). Bearings 152 permit the rotor to rotate relative to the evacuation housing. O-rings 154 and 156 seal rotor 146 from evacuation housing 150. Radial tubes or openings 158 in cap 152 communicate with central passage 134. The region around cap 142 becomes a manifold 160. Finally, nipple 162 communicates with manifold 160 and with a hose (not shown) that attaches to a suction pump.

The upper fitting 148 attaches to a drill, motor, handle or other means for rotating the tool. As the tool rotates, teeth 138 remove tissue. When nipple 162 connects to a suction pump through a hose, the manifold 160, opening 158 and central passage 134 are under low pressure. Suction draws tissue that teeth 138 cut to the distal end 164 of central passage 134.

Alternatively, openings (not shown in FIG. 5) can extend from the central passage through the housings between adjacent cutting teeth 138. With that alternative embodiment, suction from central passage 134 pulls cut particles from between adjacent teeth 138 into the central passage where they are disposed of.

FIG. 6 shows another embodiment of the cutting tool of the present invention. The principal use of this tool 180 is acetabular reaming. Total hip replacement often requires replacement of a patient's acetabular cup with an acetabular cup prosthesis. Acetabular reamers creates the properly sized region on the pelvis to receive the acetabular cup or liner.

The surgeon initiates acetabular reaming with an hemispherical reamer. Reamer 190 (FIG. 6) is such a reamer. Reaming begins through the articular cartilage and into the subchondral bone. The surgeon uses progressively larger reamers to continue exposing the cancellous bone bed as necessary. The surgeon continues reaming only until a chosen shell, which will receive the acetabular cup, can seat.

Acetabular reamers utilize a hemispherical grater head. As FIG. 6 shows, reamer 190 has a hemispherical head 192. Grater-like cutting teeth 194 are arranged in a pattern around the head 192. As reamer 190 rotates head 192, teeth 194 cut, crush, or tear pelvic tissue. Much of that tissue enters the hollow, hemispherical interior of head 192 through the openings 197 at the teeth 194. Suction that the present invention provides removes cut, crushed, or torn tissue from inside the head 192 and from outside the reamer adjacent the teeth 194.

The tool 190 of the FIG. 6 embodiment has a stem 182 extending from a proximal end 184 to a distal end 186. Stem 182 is formed of two pieces, an outer, cylindrical housing 188 and an inner housing 196 (FIG. 6). The inner housing surrounds a central passage 198.

The outer housing 188 has a fitting 200 that attaches to fitting 202 in head 192. The fittings are conventional and are of the type used with existing grater shafts and heads such as Kinamed's ATH acetabular grater shaft and head. A short cylindrical wall 204 surrounds the distal end of the outer housing 188. That cylindrical wall either attaches to the outer housing or to head 192. A sliding sleeve 206 around the outer housing can slide axially along the outer housing. The stem 182 can rotate within sleeve 206. The sleeve also has an annular shoulder 208.

A surgeon can hold sleeve 206 while the stem 182 rotates. To apply force to cutting head 192, the surgeon forces sleeve 206 distally against cylindrical wall 204. Shoulder 208 prevents the surgeon's hand from slipping off the sleeve.

The proximal end 184 of outer housing 188 has threads 210. Cap 212 at the top of inner housing 196 is above the threaded end of the outer housing 182. The outer housing threads into rotor 216. Likewise, an upper fitting 218 threads into the upper portion of rotor 216.

An evacuation housing 220 surrounds rotor 216 (FIG. 6). Bearings 222 permit rotor rotation relative to the evacuation housing. O-rings 224 and 226 seal rotor 216 from evacuation housing 220. Radial tubes or openings 228 in cap 212 communicate with central passage 198. The region around cap 212 becomes a manifold 230. Finally, nipple 232 communicates with manifold 230 and with a hose (not shown) that attaches to a suction pump.

The upper fitting 218 attaches to a drill, motor, handle or other means for rotating the tool. As the tool rotates, teeth 194 remove tissue. When nipple 232 connects to a suction pump through a hose, the manifold 230, opening 228 and central passage 198 are under low pressure. Suction draws cut, torn or crushed tissue that teeth 194 through the tooth openings 197 into the hemispherical head 192. The suction then draws the tissue into central passage 198 where it is drawn from the tool.

As numerous modifications and alternate embodiments will occur to those skilled in the art, it is intended that the invention be limited only in terms of the appended claims.

We claim:

1. A surgical method comprising:
   a. cutting tissue from of a bone with a cutting tool which has plurality of cutting teeth, each cutting tooth having a cutting edge and a back side, the cutting edge removing tissue and pushing the tissue toward the back side of the cutting tooth;
   b. applying suction to the back side of at least some of the plurality of the cutting teeth while cutting tissue to remove cut tissue from the back side.

2. A cutting tool comprising:
   a. a stem;
   b. cutting teeth extending outward from the stem, the cutting teeth having a cutting edge and a back side;
   c. a central passage at least partially through the stem,
   d. an evacuation line connected to the central passage; and
   e. a tube extending from the back side of at least one cutting tooth to the central passage.

3. The cutting tool of claim 2 wherein the cutting tool has a distal end and a proximal end; the evacuation line being connected to the proximal end of the tool.

4. The cutting tool of claim 2 wherein the cutting tool has a distal end and a proximal end; an evacuation housing receiving the stem at the proximal end of the cutting tool, the stem rotating relative to the evacuation housing, a manifold between the evacuation housing and the stem, the manifold being operably connected to the central passage; the evacuation line being connected to the evacuation housing and communicating with the manifold.

5. In a cutting tool for removing tissue, the tool having a stem, cutting teeth on the stem, the cutting teeth having a cutting edge and a back side, wherein the improvement comprises the provision of:
   a. a central passage at least partially through the stem,
   b. an evacuation line connected the central passage;
   c. a tube extending from the back side of at least one cutting tooth to the central passage.

6. The improvement of claim 5 wherein the cutting tool has a distal end and a proximal end; an evacuation housing receiving the stem at the proximal end of the cutting tool, the stem rotating relative to the evacuation housing, a manifold between the evacuation housing and the cutting tool, the manifold being operably connected to the central passage; the evacuation line being connected to the evacuation housing and communicating with the manifold.

7. The cutting tool of claim 5 wherein each cutting tooth has at least one tube extending from the back side of the cutting tooth to the central passage.

8. The cutting tool of claim 7 wherein each cutting tooth has at least two cutting faces, each cutting face having a cutting edge and a back side, the cutting tool further comprising a tube extending from the back side of more than one cutting face.

9. The cutting tool of claim 7 further comprising at least one notch on each cutting edge.

10. The cutting tool of claim 9 wherein at least two cutting teeth are axially aligned with each other, the notch on the cutting edge of one tooth being circumferentially spaced to the notch on the cutting edge of an adjacent tooth.

11. A cutting tool comprising:
    a. a stem;
    b. cutting teeth extending outward from the stem;
    c. a central passage at least partially through the stem; and
    d. suction means extending between the central passage and the outside of the stem at adjacent cutting teeth for passing material cut by the cutting teeth to the central passage.

12. The improvement of claim 11 wherein the cutting tool has a distal end and a proximal end; and rotating means between the stem and the suction means for permitting the stem to rotate relative to the suction means.

13. The improvement of claim 12, further comprising a sleeve surrounding the stem and rotating relative to the stem.

14. The improvement of claim 12 wherein the cutting teeth are on a generally hemispherical head attached to the distal end of the stem.

* * * * *